United States Patent

Planz

[19]

[11] Patent Number: 5,814,006
[45] Date of Patent: Sep. 29, 1998

[54] TEMPORARY STENT IN THE URINE PATH

[76] Inventor: Konrad Planz, Sachsenstrass 4, D-36013 Pfulda, Germany

[21] Appl. No.: 653,776

[22] Filed: May 28, 1996

[51] Int. Cl.[6] .................................................... A61M 5/00
[52] U.S. Cl. .................................................... 604/8; 623/1
[58] Field of Search ........................... 604/8, 9, 10; 623/1

[56] References Cited

U.S. PATENT DOCUMENTS

| | | | |
|---|---|---|---|
| 4,373,009 | 2/1983 | Winn | 604/8 |
| 4,729,761 | 3/1988 | White | 604/8 |
| 4,957,479 | 9/1990 | Roemer | 604/8 |
| 5,116,309 | 5/1992 | Coll | 604/8 |
| 5,229,211 | 7/1993 | Murayama et al. | 604/8 |
| 5,441,739 | 8/1995 | Kossovsky et al. | 604/8 |

*Primary Examiner*—John G. Weiss
*Assistant Examiner*—Ki Yong O
*Attorney, Agent, or Firm*—Omri M. Behr, Esq.

[57] ABSTRACT

A system is provided for the placement and maintenance of stents in the urine path comprising a stent which is made of a material which is stable in the normal environment of the urine path but becomes soluble upon change of said environment in conjunction with solution for stabilizing the pH value of urine additionally comprising other solutions for removal of the stent by providing a medically administrable substance for the alkalization of urine to enable the in situ dissolution of the stent.

17 Claims, 1 Drawing Sheet

TEMPORARY STENT IN THE URINE PATH

FIELD OF THE INVENTION

The invention is directed to an arrangement, a system utilizing same as well as a process and the use of said arrangement and system for the temporary placement of inserts into the urethral tract.

BACKGROUND OF THE INVENTION

In different ureteral conditions the provision of an ureter stent is desirable in order to ensure the free flow of urine from the kidney to the bladder. In a similar manner, it is often desirable in cases of urethral narrowing to keep the urethra open by the provisions of stents, in particular endoprotheses especially in the prostrate area.

Thus after operative procedures on and injuries to the ureter, inserts are provided in order to achieve stabilization and to facilitate healing since disturbance of the flow of urine from the kidney to the bladder can cause backup into the kidney area and thus, lead to damage of the kidney. Each retention of urine flow facilitates the infection of the urine path which in turn can affect the kidney by the generalization of the infection (Ureoseptis) which in turn can endanger the life of the patient. The purpose of a stent into the urethra/ureter is to ensure a free out-flow of urine. Indications for the provision of such a stent are all conditions in which the free out-flow is disturbed. These include tumors, as well as inflammatory illnesses, ureteral conditions, including injuries, strictures, obstructions caused by edema or seams, fistulas, perforations and retroperitoneal fibroses. Also included are stone conditions which can lead to occlusion of the ureter. Further indications would be operations on the ureter, such as ureter-ureter or ureter-intestinal anastomoses, pyeloplactic, ureter-neocystostomaty, ureterolysis, and ureterotomy. In some patients, because of poor kidney function, their general condition is so critical that an operation can seldom be performed. By the use of the ureteral stent the flow conditions can be improved. Neoplasms, for example, benign and non-benign tumors can either, per se, or through derivative swellings, hinder the out-flow.

With the increase of endoscopic techniques the placement of ureteral inserts has taken on increased importance. Since it is now possible to place a stent without an open operation and to similarly remove it, this method has become available to a larger circle of patients. The presently utilized double J or pigtailed catheters may be introduced both endoscopically as well as operatively or percutaneously. Because of their bent or rolled ends they can be maintained in the renal pelvis and similarly in the bladder. The removal of a stent occurs in the normal endoscopic way. The placement of a stent in the ureter can occur both permanently, or temporarily. In the temporary procedure the catheter is left in place up to about six weeks and thereafter removed during cystoscopy of the bladder. Indications for the temporary placement of a ureteral stent are post-operative insertion and drainage in the previously mentioned cases and in the mentioned injuries to the ureter passage. The main indications today result from the occluding ureteral presence of stones. By means of extracorporeal sound wave lithotripsy (ESWL) the treatment of such conditions is possible without operation. In order to facilitate the disintegration of the stones and to facilitate the removal of the stone residues a stent is provided to the ureter. It remains there for a few days and is thereafter removed. A further, but not very frequent indication, is pregnancy caused kidney blockage (vena ovarica syndrome) wherein the narrowing or closure of the ureter by conditions of pregnancy leads to a retention of urine in the kidney.

Problems may arise with respect to the insertion, the maintenance, and in particular however during the removal of the insert. During the removal, the end of the inserts, during cystoscopy by endoscopic means, is grabbed by pincers and the stent pulled out. This cystoscopy is an operative intrusion with its typical risks. In particular, there may be mentioned the risk of infection. By the insertion of the cystoscope, germs may be drawn into the urine path which can lead to infection. During the manipulation with the endoscope, there may be injuries to the urethra. Generally speaking, these dangers are not very large and it is particularly simple to practice cystoscopy with women. However, with older men who frequently have prostatic hyperplasia, such an intrusion can be difficult.

When in addition to injury or contamination with germs, there is the danger of urosepsis, a general infection starting with the urine paths, an illness condition which even today is associated with a high level of mortality. As a general rule, the cystoscopy for the removal of the stent is carried out on ambulatory patients. It occurs without any esthetics or further medication in order to maintain the mobility of the patient. Therefore, the intrasia can be burdensome for the patient which can turn into a problem should technical difficulties arise.

The entry to the ureteral can be carried out by means of either antegrade or retrograde cystoscopy. An intraoperative placing is also possible. Generally speaking, the ureteral stent is laid via cystoscopy.

SUMMARY

The purpose of the invention is to reduce the burden on the patient in connection with placement of a stent into the urinary tract.

In accordance with the present invention this problem is solved by placement of a stent in the urinary tract, in particular in the urethral tract or ureter tube by means of a stent (endoprosthesis) of a material which is stable in the general environment of the urinary tract but can be caused to dissolve by alterations in environmental condition.

In healthy patients, the environment and the pH in the urinary paths varies little and is generally speaking constant. It is possible, within the framework of the invention to provide a system which assists in the stabilization of the environment of the urethral path. Since the arrangement of the present invention foresees an alteration of the urinary environment from the general, that is to say, natural environment which causes the dissolution of the arrangement, the system of the present invention foresees a material for dissolving the stent particularly by administration of a medicament for the alkalinization of urine. In accordance with the process of the present invention, an arrangement as such as that described above is inserted and after predetermined time, the dissolution of the stent is caused by the direct or oral administration of the medicament. Furthermore, the invention comprises the use of the above-mentioned arrangement as well as the mentioned system for the maintenance or temporary stent in the urinary environment.

DESCRIPTION OF THE PREFERRED EMBODIMENTS

Figure 1:
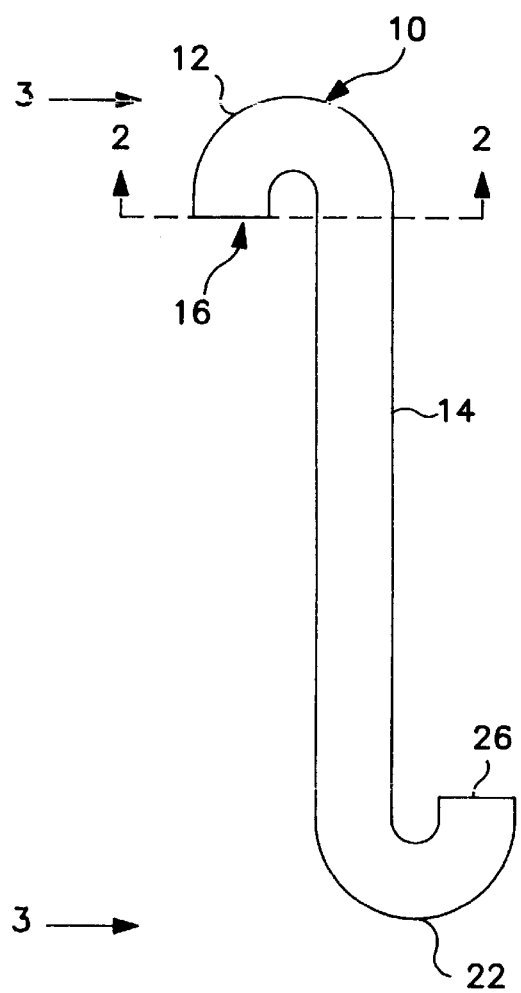
FIG. 1 is a side elevational view of a conventional double J hollow stent.
Figure 2:
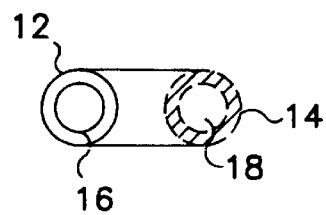
FIG. 2 is a cross-sectional view of the stent of FIG. 1 taken at 22.
Figure 3:
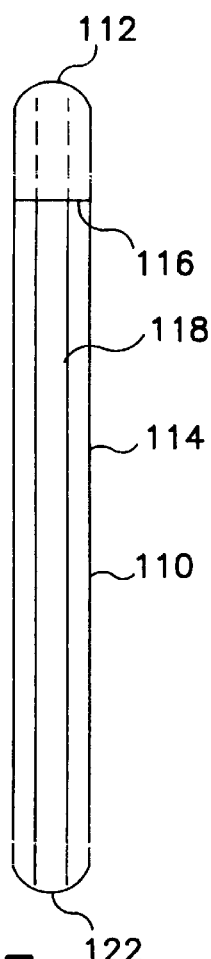
FIG. 3 is side elevational view of a stent similar to that of FIG. 1, but having an open channel rather than a closed channel as viewed from 3—3 of FIG. 1.

The stents utilized in the present invention, though of a novel material are of substantially conventional shape. FIG. 1 shows a conventional double J stent 10 having J shaped bends 12 and 22 and openings 16 and 26 connected by a hollow passage 18 running through the main body 14 of said stent. While most stents of this type are hollow this is not a requirement. Stents which are intended to merely provide support may be of the open channel type which permits the passage of urine without necessarily channeling it. Such a stent is shown in FIG. 3. The numbers being raised by 100 to signify similar segments from that in FIG. 1.

An arrangement in accordance with the present invention, in the preferred embodiment, comprises a stent which, in neutral, or lightly acidic pH, is stable, in particular the material of the stent is stable in the pH region of 5 to 6. In a further embodiment, it is provided that the material of the stent is dissolvable in a pH of between 7 and 9. In an especially preferred embodiment of the present invention, the material of the stent is a polyacrylate/polymethacrylate, especially one comprising a carboxyl group content of 7 to 12% w/w.

While such inserts may basically be straight, in the preferred embodiments they have a J or double J format. The arrangement of the present invention can be provided in the form of a short endoprothesis which either because of their basic shape or by means of dissolvable threads, can be held in the desired position during operative insertion.

The outer diameter of the stent should be less than 30, preferably between 5 to 25, most preferably between 15 and 25 French units (1 French unit is 0.333 mm. diameter). The latter being particularly favored in the case of inserts for the urethra.

Inserts for the ureter preferably have a diameter of 2 to 13 French units. The stent is suitably made as a hollow or tube formed insert.

In order to carry out insertion under radiological observation, it may, in the usual manner, be provided to yield x-ray contrast.

While dissolution may be caused by the direct provision of a suitable material into the urine tract, it is preferred to achieve the dissolution by oral the administration of a suitable medicament.

In the most preferred embodiment, there is provided a ureteral stent having a diameter of for example 8 mm made of a polyacrylate having a carboxyl group content of between 8.4 and 9.8%, such as is marketed by Belland AG, Solothurn, Switzerland, under the designation of G 100X-200 LB. This stent is endoscopically brought to the ureter via the ureteral opening of the bladder. Thereafter, a stiff catheter is pushed through the ureter in order to pass stenoses and turns. Thereafter a guide wire is passed through the catheter or along side it into ureter and the catheter removed. The stent is then threaded over the wire and pushed up the ureter by means of a positioning catheter (pusher), whereby similarly, it can be exactly positioned by means of a side thread at the end of the insert. After radiological control, the pusher, wire, and similarly the thread are removed. The thread ends curl in the bladder and the renal pelvis and thus prevent the displacement of the insert.

During the predetermined maintenance of the stent for about 14 days, the pH of the environment of urine tract is stabilized by the administration of a suitable medicament such as L-methionine hydrochloride. After fourteen days, a different medication such as potassium sodium hydrogen citrate contained in "Urolyt-U", manufactured by the Madaus Company is administered, whereby the pH value of between 5 to 6 is altered to 7 to 9 and within about 12 hours the dissolution of the ureteral stent occurs since the polymer structure is dissolved and the remaining non-toxic monomer is readily flushed out.

Alternatively, the stent may be dissolved by the direct administration of a pharmaceutically acceptable basic solution directly into the urine path. Very dilute solutions of aqueous ammonia, sodium bicarbonate or sodium hydroxide, suitably having a pH of about 7.1-about 9.5 may be employed. It is especially preferred to utilize sodium bicarbonate at about 8.4 w/w.

By means of the arrangement of the present invention, the mechanical removal of the stent at the end of treatment is no longer required. Thus, the security of the insertion is increased. During the insertion of the stent, the use of the previous employed bladder catheter can be avoided and therewith the risk of infection considerably reduced. In operative interventions into the urethral tube such as structural slitting or plastic intervention, a short non-exiting stent in the form of a support housing can aid the healing without the danger of infection with conventional bladder catheters.

By the use of the stent of the present invention, as previously mentioned, a mechanical removal thereof is no longer necessary. This leads to a decreased burden on the patient and a reduction of the above-mentioned risks.

It is claimed:

1. A stent comprising a solid member having passage means therein, for placement in the urinary tract, said member being made entirely of a material which is stable in the urine path at between pH 5 to 6, but becomes soluble upon change of the pH of said path to between pH 7 to 9.

2. The stent in accordance with claim 1 wherein said material is a polyacrylate/polymethacrylate.

3. The stent in accordance with claim 2, wherein said material has a carboxyl group content of between 7 and 12 weight %.

4. The stent in accordance with claim 1 which has a J or double J shape.

5. The stent in accordance with claim 1 which is a short, locally insertable endoprothesis.

6. The stent in accordance with claim 1 wherein the stent has a diameter of less than 30, preferably 5 to 25 French units.

7. The stent in accordance with claim 6 wherein the stent has a diameter of between 2 and 12 French units.

8. The stent in accordance with claim 6 wherein the stent has a diameter of between 15 to 25 French units.

9. The stent in accordance with claim 1 which has at least some x-ray contrast visible segments.

10. A system for the placement and maintenance of stents in the urine path of a patient comprising placement therein of a stent comprising a solid member having passage means therein, for placement in the urinary tract, said member being made entirely of a material which is stable in the urine path at between pH 5 to 6, but becomes soluble upon change of the pH of said path to between pH 7 to 9, and administering to said patient a material for stabilizing the pH value of urine at between pH 5 to 6.

11. The system in accordance with claim 10 wherein the material for stabilizing of the urine pH is orally administrable L-methionine hydrochloride.

12. The system in accordance with claim 10 additionally comprising means for removal of the stent by providing a medicinally administrable substance for the alkalization of urine to enable the in situ dissolution of said stent.

13. The system of claim 12 wherein said substance is an orally administrable substance for the alkalization of urine.

14. The system of claim 13 wherein the basic medicament is a potassium and/or sodium hydrogen citrate.

15. The system in accordance with claim 13 wherein said substance for the dissolution of the stent is a basic substance directly administrable to the urine path.

16. The system in accordance with claim 12 wherein the substance for the in situ dissolution of the stent is dilute aqueous ammonia, sodium hydroxide or sodium bicarbonate.

17. The system in accordance with claim 16 wherein the substance for the in situ dissolution of the stent is dilute aqueous ammonia, sodium hydroxide or sodium bicarbonate of pH about 7.1-about 9.5.

* * * * *